United States Patent [19]

Pugach et al.

[11] Patent Number: 5,004,839

[45] Date of Patent: Apr. 2, 1991

[54] PREPARATION OF UNSATURATED KETONES FROM ACETONE AND PARAFORMALDEHYDE (II)

[75] Inventors: Joseph Pugach, Monroeville Borough; Jeffrey S. Salek, Oakdale Borough, both of Pa.

[73] Assignee: Aristech Chemical Corporation, Pittsburgh, Pa.

[21] Appl. No.: 508,454

[22] Filed: Apr. 13, 1990

Related U.S. Application Data

[63] Continuation-in-part of Ser. No. 425,269, Oct. 23, 1989, abandoned.

[51] Int. Cl.$^5$ ............................................. C07C 45/45
[52] U.S. Cl. ................................. 568/390; 568/388; 568/345; 568/313
[58] Field of Search ............... 568/312, 313, 345, 353, 568/390, 388

[56] References Cited

U.S. PATENT DOCUMENTS

| | | | |
|---|---|---|---|
| 2,064,564 | 12/1936 | Quattlebaum, Jr. | 260/134 |
| 2,245,567 | 6/1941 | Brant et al. | 260/593 |
| 2,278,638 | 4/1942 | Barnes | 260/63 |
| 2,309,727 | 2/1943 | Barnes | 260/66 |
| 2,451,351 | 10/1948 | Mottern et al. | 260/593 |
| 2,462,031 | 2/1949 | Wittcoff | 260/333 |
| 2,549,508 | 4/1951 | Mottern | 260/586 |
| 3,578,702 | 5/1971 | Snapp, Jr. et al. | 260/486 |
| 3,592,856 | 7/1971 | Offenhauer et al. | 260/590 |
| 3,928,457 | 12/1975 | Ember | 260/593 R |
| 3,928,458 | 12/1975 | Hagemeyer, Jr. et al. | 260/593 R |
| 4,005,147 | 1/1977 | Fischer et al. | 568/390 |
| 4,035,395 | 7/1977 | Stetter et al. | 260/347.5 |
| 4,355,184 | 10/1982 | Kaku et al. | 568/31 |
| 4,374,274 | 2/1983 | Heilen et al. | 568/313 |

FOREIGN PATENT DOCUMENTS 506850   6/1939   United Kingdom ............... 568/390

OTHER PUBLICATIONS

Ai, Chem. Abst., vol. 108, 190 111,495h (1988).
Zhang et al., Chem. Abst., vol. 109, #189, 797 (1988).
Zhang et al., Chem. Abst., vol., 110 #56784r (1989).
Hays et al., "Condensation of Formaldehyde with Compounds Containing Activated Hydrogens", *J. Am. Chem. Soc.*, vol. 73, pp. 5369-5373 (Nov., 1951).

*Primary Examiner*—James H. Reamer
*Attorney, Agent, or Firm*—William L. Krayer

[57] ABSTRACT

Unsaturated ketones are produced from ketones and paraformadehyde under mild reaction conditions utilizing a catalyst comprising a halogen acid salt of a secondary amine and a nonsoluble solid oxide of an element selected from groups IB, IIIA, IVA, IVB, VA, VB, VIB and VIII of the periodic table. Temperatures of 120-150 and pressures of 700-1200 kpa are preferred; by-products may include di-unsaturated ketones such as divinyl ketone. Unsaturated ketones such as methyl vinyl ketone are useful in imparting ultraviolet sensitivity to plastics which enhances degradability.

31 Claims, No Drawings

PREPARATION OF UNSATURATED KETONES FROM ACETONE AND PARAFORMALDEHYDE (II)

This application is a continuation-in-part of our co-pending U.S. patent application Ser. No. 425,269, filed Oct. 23, 1989 now abandoned.

TECHNICAL FIELD

This invention relates to the conversion of ketones, especially acetone, to unsaturated ketones and particularly to vinyl ketones. Typical is the reaction of acetone with paraformaldehyde at temperatures of about 120–150° C. and pressures of atmospheric to about 1600 kilopascals in the presence of a solid catalyst comprising one or more oxides of elements of Groups IB, IIIA, IVA, IVB, VA, VB, VIB and VIII of the periodic table and a halogen acid salt of a secondary amine. Vinyl ketones are of current interest as a comonomer for photodegradable and biodegradable plastics and as photosensitizers, and are of conventional use as a comonomer in various plastics and resins.

BACKGROUND OF THE INVENTION

Prior to the present invention, it has been known to react acetone with formaldehyde to obtain methyl vinyl ketone. See Ember U.S. Pat. No. 3,928,457. This patent asserts that "yields of up to 82% methyl vinyl ketone, based on formaldehyde, can be expeditiously obtained." Efficiencies with respect to acetone, however, are not as good. The '457 patent requires a catalyst of phosphoric or sulfuric acid.

A general reaction for the preparation of an alpha, beta unsaturated ketone by catalytic vapor phase condensation of formaldehyde and a ketone is disclosed in U.S. Pat. No. 3,928,458. In Table VI, the use of acetone is shown; the catalyst is a silica gel.

Alpha, beta-unsaturated ketones have been prepared by reacting ketones with formaldehyde or methanol at elevated temperatures in the presence of a heterogeneous catalyst. See equation 1.

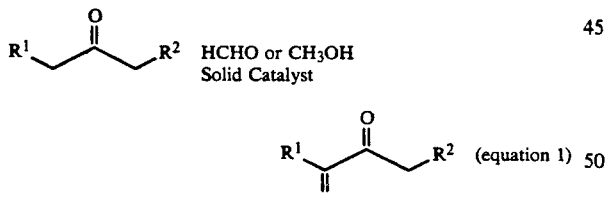

(equation 1)

Both vapor-phase and liquid-phase processes have been used to accomplish this. See U.S. Pat. No. 3,578,702 and U.S. Pat. No. 2,451,351, the latter employing a catalyst which contains oxides of metals from Groups II and V of the periodic table to react ketones with aliphatic aldehydes; see also British Patent No. 993,389.

In U.S. Pat. No. 2,549,508, Example V, methyl ethyl ketone is reacted in the vapor phase with formaldehyde in the presence of a solid mixture of zinc oxide and zirconium oxide to form methyl isopropenyl ketone.

However, these processes are generally uneconomical because of short-lived catalyst activity which results from the tendency of MVK and/or formaldehyde to polymerize on the surface of the catalyst. Consequently, frequent replacement or regeneration of the solid catalysts is necessary.

There are other liquid-phase processes for producing MVK discussed in the literature. One process relates to initially generating 3-keto-1-butanol from acetone and aqueous formaldehyde. See U.S. Pat. No. 3,544,634. MVK is produced by dehydration in the presence of aluminum oxide.

This particular process is limited because MVK is not formed directly and a mixture of polymethylol compounds is formed along with the desired keto-alcohol which must be separated. Another disclosure concerns generation of MVK from acetone, aqueous formaldehyde and a strong acid ($H_2SO_4$, $H_3PO_4$, HCl, HBr, HI or p-toluenesulfonic acid). See previously mentioned U.S. Pat. Nos. 3,928,457 and U.S. Pat. No. 2,848,499. The U.S. Pat. No. 2,848,499 method requires relatively harsh reaction conditions of temperature, pressure and acid dissociation constant ($10^{-4}$ or greater) while still only resulting in acetone conversions of less than 10%.

The literature also teaches the separate use of secondary amines and strong acid or weak acid salts of secondary amines for the reaction of ketones and, primarily, aldehydes, with aqueous formaldehyde (monomeric) to form the corresponding vinyl aldehyde and ketones (see Ai, M. J., *Catal.*, 1987, 106, 2734; Ueda, W. Yokoyama, T., Moro-Oka, Y., Ikawa, T., *J. Chem. Soc., Chem., Commun*, 1984, 39.; Gutsche, D. C., Nam., K.C., *J. Am. Chem. Soc.*, 1988, 110, 6153; U.S. Pat. Nos. 4,275,242, 4,343,239, 4,406,079 and 4,496,770). A tertiary amine is used in U.S. Pat. No. 3,077,500.

The reader may also be interested in reviewing U.S. Pat. Nos. 4,374,374, 3,928,450 and 3,701,798. The '798 patent uses an oxide of a rare earth metal as a catalyst.

The inventors herein have recently (on June 19, 1989) filed a U.S. patent application Ser. No. entitled "Preparation of Unsaturated Ketones" on the use of paraformaldehyde as a reactant with various ketones to add one or more unsaturated groups thereto, noting particularly that paraformaldehyde has not been used in such reactions in the past. Said application is incorporated herein by reference. It should be noted that the catalyst employed in that case is different from the catalyst herein, being an acid salt of a secondary amine in combination with a small amount of carboxylic acid. As will be seen below, the catalyst we employ herein is an acid salt of a secondary amine in combination with certain nonsoluble oxides. The oxide may be used on an adsorbtive support.

SUMMARY OF THE INVENTION

Our invention is a method of making an $\alpha, \beta$ unsaturated ketone (or, in the case of an $\alpha, \beta$ unsaturated feed material, an $\alpha, \beta, \gamma, \delta$ unsaturated ketone) comprising reacting paraformaldehyde with a ketone of the formula

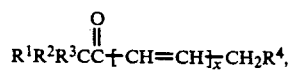

where x is 0 or 1, in the presence of a secondary amine catalyst, a halogen acid, preferably in an amount about equimolar to the amine, and a solid catalyst selected from the group consisting of nonsoluble oxides of elements (as further explained below) of Groups IB, IIIA, IVA, IVB, VA, VB, VIB and VIII of the periodic table, specifically the periodic table as published in the 61st Edition of Chemical Rubber Company's Handbook of Chemistry and Physics. If x is 1, the resulting compound will be

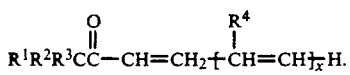

The ratio of ketone to formaldehyde (which is in the form of paraformaldehyde) is not critical, but is advantageously a molar ratio of about 10:1 to about 1:10, preferably about 3:1 to about 1:3. In the higher ratios within this range, formaldehyde conversions of 95–100% are obtained with an equimolar amount of acetone (or other ketone feed) being consumed, while selectivities to vinyl ketones are 70–100%. Ketone conversions approaching 100% based on paraformaldehyde consumption are common in the higher ratios within these ranges. At lower ratios, ketone conversions of 30–50% are observed with selectivities to vinyl ketones based on the starting ketone of 70–80%. Temperatures may range from about 50° C. to about 250° C., preferably 120–150° C., and pressures from atmospheric to about 1600, preferably 775–1480 kilopascals. Use of an inert atmosphere such as argon or nitrogen is preferred but not essential. Inert solvents may be used if desired to dilute the reactants but are not necessary. In batch processing, the reaction should be conducted for at least 0.25 hours, with 1–2 hours being preferred, depending on the other conditions. Reaction times beyond ten hours confer no further advantage. A stabilizer such as hydroquinone may also be used as known in the art to prevent polymerization of the unsaturated product.

In the above general description, $R^1$, $R^2$, $R^3$ and $R^4$ may be independently chosen hydrogen or alkyl or aromatic groups having 1 to about 15 carbon atoms, including unsaturated groups provided that if both $R^1$ and $R^2$ are unsaturated, they should have a total of at least 4 carbon atoms, and also provided that $R^1$, $R^2$, $R^3$ and/or $R^4$ may form part of the same carbon or heterocyclic ring which may have substitutions, the total number of carbon atoms thereof being up to about 30.

The halogen acid may be added separately or integrally with the amine in the form of an addition salt, i.e.

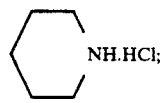

we consider such separate or integral additions to be equivalent. Suitable halogen acids include any of the halogen acids.

Thus, a general reaction for a simple unsaturated ketone may be depicted as:

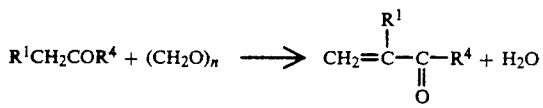

The designation $(CH_2O)_n$ denotes paraformaldehyde, which normally is sold as a solid having about 8 to about 100 monomer units, i.e., n=8 to 100.

It is understood that a di-unsaturated ketone may be made in the case when $R^4$ is a group $CH_2R^7$ so that

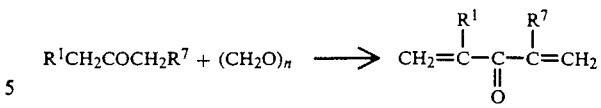

Our invention has the advantage that the presence of water is minimized, in addition to obtaining excellent yields and selectivities under relatively mild conditions, employing a metal oxide or similar co-catalyst which may be recycled or reused relatively easily. It was surprising and unexpected how well paraformaldehyde worked (in the presence of our catalyst) since it is assumed in the literature that paraformaldehyde decomposes to the monomer (the normally reactive species) only in the presence of strong acids (see Bevington, T., Q. Rev., Chem. Soc., 1952, 6, 141.; U.S. Pat. Nos. 4,340,767; 3,925,488 and 3,026,264; Japan Patent No. 59 55,849; Process Economics Program (Formaldehyde; Report No. 23), Stanford Research Institute, Menlo Park, California, 1967, pp. 45–46, 154. 1, 3, 5-Trioxane (the trimer of formaldehyde) also gave poor results with our catalyst system, again demonstrating the uniqueness of the paraformaldehyde/catalyst combination. While the reaction itself generates water, our process minimizes the amount of water present. Moreover, and perhaps most important, our process produces no detectable acetone condensation products such as mesityl oxide.

Examples of suitable nonsoluble oxides for use in our catalyst are niobium oxide, tungsten oxide, hafnium oxide, iron oxide, nickel oxide, titanium oxide, vanadium oxide, and aluminum oxide. The oxide is used together with a halogen acid salt of a secondary amine in a weight ratio of amine (exclusive of the associated acid) to oxide of from about 0.5:1 to about 10:1. The reaction is preferably conducted in the presence of an inert gas.

By nonsoluble, we mean not soluble under the conditions of the reaction in either an organic or inorganic medium which is present. It will be seen in the examples below that the oxides also include the insoluble acids of the oxides which can be formally thought of as the hydration products of the oxides. Examples of these acids are: niobic acid, tungstic acid, silicic acid and the like. Accordingly, we use the phrase "nonsoluble oxide of an element" of the designated periodic table groups to describe the materials we employ; fragments such as $WO_4$ must be present as nonsoluble compounds. Certain insoluble phosphates, as seen in the $BPO_4$ example, are operable in our invention; however, we do not employ phosphoric acid or any of the readily soluble phosphates such as trisodium phosphate or any other soluble alkali metal compounds. Thus, the oxygen-containing compounds we employ are the nonsoluble oxides of elements of Groups IB, IIIA, IVA, IVB, VA, VB, VIB and VIII of the periodic table.

When we speak of the medium which is present and in which the solid catalyst is not soluble, we refer typically to the liquid reactants such as the ketone feed, water produced as a by-product, and the desired ketone products. Other potential solvent media are aliphatic hydrocarbons, aromatic hydrocarbons, ethers, and nitriles. However, solvents are not necessary. We intend for our solid catalysts to be soluble in none of these under the conditions of the reaction. The potential solvents in the reaction mixture may be generally defined as those which are non-reactive under the reaction conditions.

A preferred catalyst is niobium oxide. More generally, oxides of metals of the groups IVB, VB, VIB, and VIII are preferred.

The solid catalyst may be utilized in a bed or in a slurry; the reaction may be conducted continuously or batch-wise.

The amine catalyst may comprise a reaction product, i.e. a combination of a secondary amine and an acid salt such as hydrochloric acid. Examples of suitable amines are piperidine, dibutyl amine, diphenylamine, piperazine, dioctyl amine, diethyl amine, dipropyl amine, pentyl n-butyl amine, diisobutylamine, dihexyl amine and the halogen acid salts thereof.

The amine catalyst should be present in an amount representing from about 0.01 to about 0.1 equivalent per equivalent of the starting ketone feed.

In the Examples below, the results are shown for various experiments including some conducted according to the general procedure which follows.

The procedure used for vinylation of acetone with formaldehyde was:

A reaction mixture containing 80g acetone (3.0 equiv.), 13.8g paraformaldehyde (formally 1.0 equiv.), 0.08g hydroquinone (0.0005 equiv.), 4.17g piperidine hydrochloride; 0.025 equiv.) was charged along with 3 ml of 1,4-dioxane and about 0.01 equiv. of the metal oxide shown in Table I into a pressure reactor (Parr autoclave) having a nitrogen or argon atmosphere at about 100-250 psig with agitation. After a reaction time of about one to two hours at a temperature of about 135° C., the charge was rapidly cooled in an ice-water bath.

GC analysis commonly revealed acetone conversions of 30-80% based on reacted formaldehyde and MVK and DVK selectivities based on reacted acetone of 80-97% and 1-10% respectively.

Atmospheric fractional distillation recovers both acetone and MVK, each at greater than 99% purity.

TABLE I

| GROUP | OXIDE | CONVERSION (%) | % MVK SEL. | % DVK SEL. |
| --- | --- | --- | --- | --- |
| IIIB | $Y_2O_3$ | 0 | 0 | 0 |
| IVB | $TiO_2$ | 75 | 83 | 7 |
| IVB | $Ti_2O_3$ | 63 | 95 | 5 |
| IVB | $ZrO_2$ | 60 | 90 | 10 |
| IVB | $HfO_2$ | 70 | 87 | 6 |
| VB | $Nb_2O_5$ | 76 | 92 | 8 |
| VIB | $Cr_2O_3$ | 52 | 95 | 5 |
| VIB | $H_2WO_4$ | 63 | 93 | 7 |
| VIIB | $MnO_2$ | 42 | 14 | 0 |
| VIIIB | $Fe_2O_3$ | 67 | 53 | 2 |
| VIIIB | $\sim Co_3O_4$ | 42 | 92 | 0 |
| VIIIB | $NiO$ | 67 | 95 | 5 |
| IB | $CuO$ | 33 | 96 | 0 |
| IIB | $CdO$ | 52 | 20 | 1 |
| IIIA | $BPO_4$ | 75 | 75 | 6 |
| IIIA | $Al_2O_3$ | 50 | 97 | 3 |
| IVA | $SiO_2$ | 60 | 93 | 7 |
| IVA | Silica Gel | 60 | 96 | 4 |
| VA | $Bi_2O_3$ | 27 | 90 | 1 |
| VB | $Ta_2O_5$ | 70 | 66 | 4 |
| Rare Earth | $CeO_2$ | 24 | 98 | 2 |

For the example of niobium oxide ($Nb_2O_5$), the catalyst was prepared as follows:

To a 2-liter three-necked round bottom flask equipped with a mechanical stirrer, a thermometer and a dropping funnel, was added 500ml of deionized water. Then 100g of $NbCl_5$ (obtained from Cerac, Inc.) was slowly added to the water with good agitation, and at such a rate that the temperature of the mixture did not go above 50° C. After addition was complete, stirring was continued for an additional 0.5 hours at which point 257 ml of 28% aqueous ammonia was added in the period of 0.5 hours. Stirring of the slurry was continued for an additional 0.5 hours, and the slurry was then filtered through a coarse fritted vacuum funnel. The cake so collected was then put back into the flask and washed with 500 ml of fresh deionized water with good stirring for 15 minutes and the filtration and washing procedure was repeated until the pH of the final wash solution was 6.5-7.0. The hydrated niobium oxide was then dried to a constant weight in a drying oven at 150° C. Treatments at higher temperatures were done for three hours in a muffle furnace.

Conditions for the examples in Table II were similar to those of Table I except for variations a-o noted below; in each case in Table II, unless otherwise noted as in d and e, the catalyst used was niobium oxide prepared as recited above.

TABLE II

| VARIATION | CONVERSION (%) | % MVK SEL. | % DVK SEL. |
| --- | --- | --- | --- |
| a | 90 | 95 | 5 |
| b | 53 | 18 | 0 |
| c | 51 | 21 | 0 |
| d | 66 | 90 | 8 |
| e | 69 | 80 | 6 |
| f | 90 | 97 | 3 |
| g | 24 | 94 | 6 |
| h | 72 | 66 | 2 |
| i | 15 | 13 | 0 |
| j | 39 | 92 | 2 |
| k | 51 | 67 | 1 |
| l | 15 | 0 | 0 |
| m | 50 | 89 (VIP) | — |
| n | 75 | 90 (PVK) | — |
| o | 53 | 27 | 1 | a - Acetone-to-formaldehyde molar ratio increased to 4:1
b - Neutral piperidine rather than piperidine hydrochloride was used as amine catalyst
c - $Nb_2O_5$ concentration increased 4-fold (0.04 equiv. relative to starting ketone feed)
d - $Nb_2O_5$ drying temperature of 150° C. for 3 hours
e - $Nb_2O_5$ drying temperature of 400° C. for 3 hours
f - Acetone-to-formaldehyde molar ratio increased to 5:1
g - Reaction time decreased to 0.25 hours
h - Reaction time increased to 6.0 hours
i - Amine catalyst absent
j - Aqueous formaldehyde (37 wt %) rather than paraformaldehyde used
k - Reaction temperature increased to 175° C.
l - 1,3,5-Trioxane rather than paraformaldehyde used
m - Isophorone substituted for acetone feed; conversion to vinylated isophorone (VIP)
n - Acetophenone substituted for acetone feed; conversion to phenyl vinyl ketone (PVK)
o - Piperidine hydrochloride without any oxygen-containing catalyst.

Additional experiments were run under the physical conditions described for Table I as follows:

1. Using a 3:1 equivalent ratio of acetone to paraformaldehyde, an Nb2O5 catalyst (0.01 equiv.) and

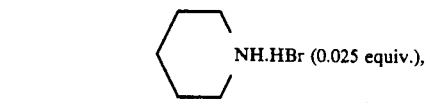
NH.HBr (0.025 equiv.), conversion of acetone was 52%, with 70% methyl vinyl ketone selectivity and 5% divinyl ketone selectivity.

2. Under the same conditions, solid catalyst and ratios of one above but substituting

 NH.HF for the amine catalyst,

53% conversion was obtained with 67% MVK selectivity and 4% DVK selectivity.

3. Using a 3:1 equivalent ratio of methyl ethyl ketone (MEK) to paraformaldehyde, and the same quantities of catalyst and reactants recited in one above but with the hydrochloric acid salt of piperidine as the amine catalyst, about 70-90% of the MEK was converted, with about 50-70% selectivity to methyl isopropenyl ketone (MIPK) and 20-30% selectivity to ethyl vinyl ketone (EVK).

4. Experiment 3 above was repeated with a 4:1 ratio of MEK to paraformaldehyde instead of 3:1. MEK conversion was about 90-100%; selectivities were about 50-70% MIPK and about 20-30% EVK.

We claim:

1. Method of making a compound of the formula

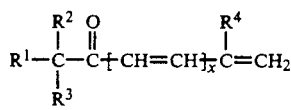

comprising reacting a ketone of the formula

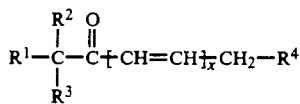

with paraformaldehyde in the presence of a secondary amine catalyst, a halogen acid, and a solid catalyst selected from the group consisting of nonsoluble oxides of elements of Groups IB, IIIA, IVA, IVB, VA, VB, VIB and VIII of the periodic table, where $R^1$, $R^2$, $R^3$ and $R^4$ are independently selected from hydrogen, alkyl and aromatic groups having 1 to about 15 carbon atoms including unsaturated groups provided that if both $R^1$ and $R^2$ are unsaturated, they should have a total of at least 4 carbon atoms and also provided that $R^1$, $R^2$, $R^3$ and $R^4$ may form parts of the same carbon or heterocyclic ring which may have substitutions, the total number of carbon atoms thereof being up to about 30, and x is 0 or 1.

2. Method of claim 1 wherein the ratio of ketone to paraformaldehyde is about 10:1 to about 1:10.

3. Method of claim 1 wherein the ratio of ketone to paraformaldehyde is about 3:1 to about 1:3.

4. Method of claim 1 wherein the temperature is maintained in the range of about 50° C. to about 250° C.

5. Method of claim 1 wherein the pressure is maintained at about 775-1480 kilopascals.

6. Method of claim 1 wherein the amine catalyst is present in an amount from about 0.01 equivalent to about 0.1 equivalent with respect to the ketone reactant.

7. Method of claim 1 wherein the halogen acid is present in the form of a salt of the amine catalyst.

8. Method of claim 1 wherein the solid catalyst is present in an amount from about 0.0025 to about 0.1 equivalent with respect to the ketone reactant.

9. Method of claim 1 wherein the solid catalyst is present in an amount from about 0.01 to about 0.025 equivalent with respect to the ketone reactant.

10. Method of claim 1 wherein the ketone feed is acetone.

11. Method of claim 1 wherein the ketone feed is isophorone.

12. Method of claim 1 wherein the ketone feed is acetophenone.

13. Method of making an unsaturated ketone comprising reacting paraformaldehyde with a ketone in the presence of a catalyst which is a halogen acid salt of a secondary amine and a solid catalyst selected from the group consisting of nonsoluble oxides of elements of Groups IB, IIIA, IVA, IVB, VA, VB, VIB and VIII of the periodic table.

14. Method of claim 13 wherein the solid catalyst is present in a bed.

15. Method of making methyl vinyl ketone comprising reacting paraformaldehyde with acetone in the presence of an effective amount of a catalyst comprising a halogen acid salt of a secondary amine and a solid catalyst selected from the group consisting of nonsoluble oxides of elements of Groups IB, IIIA, IVA, IVB, VA, VB, VIB and VIII of the periodic table.

16. Method of claim 15 wherein the solid catalyst is present in a bed.

17. Method of claim 15 wherein the solid catalyst is niobium oxide.

18. Method of making phenyl vinyl ketone comprising reacting paraformaldehyde with acetophenone in the presence of an effective amount of a catalyst comprising a halogen acid salt of a secondary amine and a solid catalyst selected from the group consisting of nonsoluble oxides of elements of IB, IIIA, IVA, IVB, VA, VB, VIB and VIII of the periodic table.

19. Method of claim 18 wherein the solid catalyst is niobium oxide.

20. Method of claim 18 wherein the ratio of acetophenone to paraformaldehyde is about 3:1 to about 1:3.

21. Method of making a vinylated isophorone comprising reacting paraformaldehyde with isophorone in the presence of an effective amount of a catalyst comprising a halogen acid salt of a secondary amine and a solid catalyst selected from the group consisting of nonsoluble oxides of elements of Groups IB, IIIA, IVA, IVB, VA, VB, VIB and VIII of the periodic table.

22. Method of claim 21 wherein the solid catalyst is niobium oxide.

23. Method of claim 21 wherein the ratio isophorone to paraformaldehyde is about 3:1 to about 1:3.

24. Method of making methyl isopropenyl ketone comprising reacting paraformaldehyde with methyl ethyl ketone in the presence of an effective amount of a catalyst comprising a halogen acid salt of a secondary amine and a solid catalyst selected from the group consisting of nonsoluble oxides of elements IB, IIIA, IVA, IVB, VA, VB, VIB, and VIII of the periodic table.

25. Method of claim 24, wherein the solid catalyst is niobium oxide and the ratio of methyl ethyl ketone to paraformaldehyde is greater than one.

26. Method of claim 24 wherein the amine catalyst is in the form of a hydrochloric acid salt.

27. Method of making ethyl vinyl ketone comprising reacting paraformaldehyde with methyl ethyl ketone in the presence of an effective amount of a catalyst comprising a halogen acid salt of a secondary amine and a solid catalyst selected from the group consisting of nonsoluble oxides of elements IB, IIIA, IVA, IVB, VA, VB, VIB, and VIII of the periodic table.

28. Method of claim 27 wherein the solid catalyst is niobium oxide and the ratio of methyl ethyl ketone to paraformaldehyde is greater than one.

29. Method of claim 27 wherein the amine catalyst is in the form of a hydrochloric acid salt.

30. Method of making methyl isopropenyl ketone comprising reacting paraformaldehyde with methyl ethyl ketone in the presence of an effective amount of a catalyst comprising a secondary amine, a halogen acid, and a solid catalyst selected from the group consisting of nonsoluble oxides of elements IB, IIIA, IVA, IVB, VA, VB, VIB, and VIII of the periodic table.

31. Method of claim 30 wherein the halogen acid is hydrochloric acid.

* * * * *

UNITED STATES PATENT AND TRADEMARK OFFICE
CERTIFICATE OF CORRECTION

PATENT NO. : 5,004,839

DATED : April 2, 1991

INVENTOR(S) : Joseph Pugach and Jeffrey S. Salek

It is certified that error appears in the above-identified patent and that said Letters Patent is hereby corrected as shown below:

Column 2, line 27, "U.$." should be -- U.S. --;
        line 34, after "application" delete "Ser. No.".

Column 3, line 6, change "$R^1R^2R^3C\overset{O}{\overset{\|}{C}}-CH=CH_2\overset{R^4}{(CH=CH)_x}H$"

to -- $R^1R^2R^3C\overset{O}{\overset{\|}{C}}-CH=CH_2-\overset{R^4}{(CH=CH)_x}H$ --.

Column 3, line 49, in the diagram, "NH.HCl" should be -- NH·HCl --.

Column 6, line 57, "Nb205" should be -- $Nb_2O_5$ --;

line 61, in the diagram, "NH.HBr (0.025 equiv.)," should be
                -- NH·HBr (0.025 equiv.), --.

Column 7, line 4, in the diagram "NH.HF for the amine catalyst," should be
                -- NH·HF for the amine catalyst,--.

Signed and Sealed this

Eighth Day of September, 1992

Attest:

DOUGLAS B. COMER

*Attesting Officer*          *Acting Commissioner of Patents and Trademarks*